| United States Patent [19] | [11] Patent Number: 4,537,987 |
| Schneider et al. | [45] Date of Patent: Aug. 27, 1985 |

[54] PREPARATION OF PURE MONOESTERS OF ADIPIC ACID

[75] Inventors: Heinz-Walter Schneider; Wolfgang Richter, both of Ludwigshafen; Walter Disteldorf, Wachenheim; Rudolf Kummer, Frankenthal, all of Fed. Rep. of Germany

[73] Assignee: BASF Aktiengesellschaft, Fed. Rep. of Germany

[21] Appl. No.: 629,766

[22] Filed: Jul. 11, 1984

[30] Foreign Application Priority Data

Jul. 14, 1983 [DE] Fed. Rep. of Germany ....... 3325372

[51] Int. Cl.³ .............................................. C07C 67/38
[52] U.S. Cl. .................................... 560/193; 502/171; 560/190; 560/204
[58] Field of Search ....................... 560/204, 190, 193; 502/171

[56] References Cited

U.S. PATENT DOCUMENTS

| 3,530,168 | 9/1970 | Biale ................................. 560/204 X |
| 4,256,909 | 3/1981 | Kummer et al. ..................... 560/204 |
| 4,314,071 | 2/1982 | Babler ................................. 560/127 |
| 4,404,394 | 9/1983 | Isogai et al. .......................... 560/204 |

*Primary Examiner*—Natalie Trousof
*Assistant Examiner*—Vera C. Clarke
*Attorney, Agent, or Firm*—Keil & Weinkauf

[57] ABSTRACT

Pure monoesters of adipic acid are prepared by a process in which (a) a pentenoate is reacted with carbon monoxide and hydrogen at from 90° to 140° C. and under from 5 to 300 bar in the presence of a carbonyl complex of cobalt or of rhodium, and a 5-formylvalerate is separated off, and (b) the 5-formylvalerate thus obtained is oxidized with molecular oxygen, or with a gas containing this, at from 20° to 100° C. under from 1 to 10 bar.

5 Claims, No Drawings

PREPARATION OF PURE MONOESTERS OF ADIPIC ACID

In conventional processes for the preparation of monoesters of adipic acid, adipic acid is used as a starting material, and the intention is to interrupt the esterification at the monoester stage. In the process disclosed in U.S. Pat. No. 4,314,071, adipic acid is esterified with an alcohol in aqueous solution in the presence of sulfuric acid as a catalyst, and a non-polar solvent is used to extract the monoester immediately at the rate at which it is formed. The reaction is carried out in the course of 5 days, which makes it considerably time-consuming. Moreover, the adipic monoester obtained from the extract has a purity of only 96%, and a complicated working up procedure is required in order to obtain a purer monoester of adipic acid.

In the process described in German Laid-Open Application DOS No. 2,404,359, too, adipic acid is used as a starting material, and is esterified with an alcohol in the presence of not less than one mole of water per mole of adipic acid. The yields of monoesters of adipic acid are unsatisfactory because substantial amounts of diesters of adipic acid are obtained as by-products. In order to obtain pure monoesters of adipic acid, these diesters have to be separated off in an expensive procedure.

It is an object of the present invention to prepare monoesters of adipic acid in high yield and high purity.

We have found that this object is achieved by a process for the preparation of pure monoesters of adipic acid, wherein (a) a pentenoate is reacted with carbon monoxide and hydrogen at from 90° to 140° under from 5 to 300 bar in the presence of a carbonyl complex of cobalt or of rhodium, and a 5-formylvalerate is separated off, and (b) the 5-formylvalerate thus obtained is oxidized with molecular oxygen, or with a gas containing this, at from 20° to 100° C. under from 1 to 10 bar.

The novel process has the advantage that it gives high yields, and the adipic monoesters are obtained in a purity of >99%.

The starting compound used is a pentenoate, for example an alkyl ester of 1 to 12 carbon atoms, a cycloalkyl ester of 5 to 12 carbon atoms, an alkaryl ester of 7 to 9 carbon atoms or a phenyl ester. Alkyl pentenoates are preferably used, particularly those derived from an alkanol of 1 to 4 carbon atoms. Advantageously, 4-pentenoates and/or 3-pentenoates are used. Examples of suitable pentenoates are methyl 4-pentenoate, ethyl 4-pentenoate, propyl 3-pentenoate, butyl 3-pentenoate, octyl 4-pentenoate, cyclohexyl 3-pentenoate, benzyl 4-pentenoate and phenyl 3-pentenoate.

The reaction is carried out using a mixture of carbon monoxide and hydrogen, advantageously in a molar ratio of from 10:90 to 50:50, in particular 10:40.

The hydroformylation is carried out at from 90° to 140° C., but advantageously at from 100° to 120° C. when a rhodium carbonyl complex is used. Furthermore, the pressure is maintained at 5-300 bar, but advantageously at 5-20 bar when a rhodium carbonyl complex is used.

The hydroformylation catalyst used is a carbonyl complex of rhodium or cobalt. The carbonyl complexes can be prepared before the reaction, or are advantageously formed in situ from a salt of rhodium or cobalt, for example their fatty acid salts, such as cobalt acetate or rhodium acetate. Advantageously, the rhodium or cobalt carbonyl complex is additionally modified by a tertiary phosphine or tertiary phosphite. Suitable examples are tertiary alkyl- and arylphosphines and tertiary alkyl and aryl phosphites. Triphenylphosphine, substituted triarylphosphines, such as tritolylphosphine, and alkyldiarylphosphines, such as hexyldiphenylphosphine, are preferably used.

The rhodium concentration is advantageously from 50 to 500 ppm, based on the reaction mixture and calculated as metal. Modification of the carbonyl complexes of rhodium with the stated phosphines or phosphites has proven particularly useful. Advantageously, the phosphine or phosphite is used in a 3-fold to 100-fold molar excess, based on rhodium.

If cobalt carbonyl catalysts are used, modification with phosphines and phosphites can be dispensed with, particularly when the hydroformylation is carried out using a 3-pentenoate as obtained, for example, directly in the reaction of butadiene with carbon monoxide and an alkanol in the presence of a cobalt carbonyl complex. Reaction mixtures obtained in this manner are advantageously hydroformylated using a cobalt carbonyl catalyst without further additives, at from 100° to 140° C. and under from 150 to 200 bar.

It is also possible for solvents to be present, such as liquid aromatic hydrocarbons, e.g. toluene or xylene, carboxylates, e.g. acetates, butyrates or valerates, or high-boiling condensates as formed in the reaction itself.

The reaction mixture obtained in the hydroformylation of the pentenoates contains, in addition to unreacted pentenoates, the catalyst used, the 5-formylvalerate produced as the desired product, and by-products such as 4-formylvalerates, valerates, hydroxycaproates and high-boiling condensates. The products in these reaction mixtures are first separated from the catalyst, for example by distillation or extraction, and are then isolated by fractional distillation. The 5-formylvalerate obtained in this way is used for the oxidation in the second stage.

The oxidation of the 5-formylvalerate is carried out at from 20° to 100° C., advantageously from 50° to 80° C., under from 1 to 10 bar, using molecular oxygen or a gas which contains this. The gas containing molecular oxygen can also contain, for example, not more than 80 vol % of inert gases, such as nitrogen, carbon dioxide or noble gases. As a rule, the oxidation takes place in the absence of a catalyst, but can be accelerated by adding a catalyst, such as an alkali metal hydroxide, e.g. potassium hydroxide or sodium hydroxide, in an amount of from 0.001 to 0.5% by weight, or a salt of cobalt or manganese, e.g. cobalt acetate or manganese acetate, in an amount of from 0.001 to 0.1, preferably from 0.02 to 0.08, % by weight, calculated as metal.

Distillation of the resulting reaction mixture gives an adipic monoester which is free of diesters, adipic acid and high-boiling components.

Adipic monoesters which are obtainable by the process of the invention are useful for the preparation of sebacates by the Kolbe synthesis.

The Example which follows illustrates the process according to the invention.

EXAMPLE 360 g of a mixture of methyl pentenoates which contains 342 g (3 moles) of methyl 4-pentenoate are dissolved in 600 ml of toluene in a high pressure vessel having a capacity of 2 liters. 70.2 g (268 millimoles) of triphenylphosphine and 108 mg (1.04 millimoles) of rhodium in the form of the complex HRhCOL$_3$ (L=triphenylphosphine) are added as a catalyst. The reaction mixture is heated to 110° C. and then brought to 8 bar with a mixture of 80 vol % of hydrogen and 20 vol % of carbon monoxide. When the pressure falls below 7 bar during the reaction, it is brought to 8 bar once again by forcing in an equimolar mixture of hydrogen and carbon monoxide. After 2 hours, the reaction is terminated and the reaction mixture is worked up by distillation. This gives the following:

unreacted methyl pentenoate: 81.3 g (18.5%)
methyl valerate: 9.1 g (2.6%)
methyl 4-formylvalerate: 26.8 g (6.2%)
methyl 5-formylvalerate: 310.2 g (71.8%)
methyl hydroxycaproate: 2.2 g (0.5%)
high-boiling condensates: 1.7 g (0.4%)

The yield in the hydroformylation is 71.8%, and the selectivity with respect to the 5-formylvalerate is 88.1%.

288 g (2 moles) of the methyl 5-formylvalerate obtained as described above are oxidized in a bubble column in the course of 6 hours under atmospheric pressure (1 bar) and at 50° C. by passing in oxygen. The conversion achieved in this procedure is >99%. The resulting reaction mixture is distilled in a packed column under 2 mbar and at 126° C. to give 307 g of monomethyl adipate in a purity of >99%. The yield in the oxidation is 95.9%.

We claim:

1. A process for the preparation of a pure monoester of adipic acid, wherein
   (a) a pentenoate is reacted with carbon monoxide and hydrogen at from 90° to 140° C. and under from 5 to 300 bar in the presence of a carbonyl complex of cobalt or of rhodium, said pentenoate being an alkyl ester of 1-12 carbon atoms, a cycloalkyl ester of 5-12 carbon atoms, an alkaryl ester of 7-9 carbon atoms or a phenyl ester, and a 5-formylvalerate is separated off, and
   (b) the 5-formylvalerate thus obtained is oxidized with molecular oxygen, or with a gas containing this, at from 20° to 100° C. under from 1 to 10 bar.

2. A process as set forth in claim 1, wherein a C$_1$-C$_4$-alkyl 3-pentenoate or a C$_1$-C$_4$-alkyl 4-pentenoate or a mixture of a C$_1$-C$_4$-alkyl 3-pentenoate and a C$_1$-C$_4$-alkyl 4-pentenoate is used.

3. A process as set forth in claim 1, wherein a rhodium carbonyl complex modified with a tertiary phosphine or with a tertiary phosphite is used as the catalyst.

4. A process as set forth in claim 1, wherein a 3-pentenoate is converted in the presence of a cobalt carbonyl complex.

5. The process of claim 1, wherein the pentenoate is elected from the group consisting of methyl 4-pentenoate, ethyl 4-pentenoate, propyl 3-pentenoate, butyl 3-pentenoate, octyl 4-pentenoate, cyclohexyl 3-pentenoate, benzyl 4-pentenoate and phenyl 3-pentenoate.

* * * * *

UNITED STATES PATENT AND TRADEMARK OFFICE
CERTIFICATE OF CORRECTION

PATENT NO.    : 4,537,987

DATED         : August 27, 1985

INVENTOR(S)   : Heinz-Walter SCHNEIDER et al.

It is certified that error appears in the above-identified patent and that said Letters Patent is hereby corrected as shown below:

CLAIM 5, Column 4, Line 25 "elected" should be

--selected--.

Signed and Sealed this

Twenty-sixth Day of November 1985

[SEAL]

Attest:

DONALD J. QUIGG

Attesting Officer

Commissioner of Patents and Trademarks